(12) United States Patent
Knoll

(10) Patent No.: US 6,450,972 B1
(45) Date of Patent: Sep. 17, 2002

(54) SENSOR SYSTEM FOR MEASURING PRESSURE PROFILES

(76) Inventor: Meinhard Knoll, Geschwister-Scholl-Strasse 9, D-48565 Steinfurt (DE)

(*) Notice: Subject to any disclaimer, the term of this patent is extended or adjusted under 35 U.S.C. 154(b) by 0 days.

(21) Appl. No.: 09/445,533
(22) PCT Filed: Jun. 5, 1998
(86) PCT No.: PCT/DE98/01563
§ 371 (c)(1), (2), (4) Date: Feb. 29, 2000
(87) PCT Pub. No.: WO98/56292
PCT Pub. Date: Dec. 17, 1998

(30) Foreign Application Priority Data

Jun. 7, 1997 (DE) .......................... 197 24 001

(51) Int. Cl.⁷ ............................... A61B 5/00
(52) U.S. Cl. ..................................... 600/561
(58) Field of Search ........................... 600/561

(56) References Cited

U.S. PATENT DOCUMENTS

| | | | |
|---|---|---|---|
| 3,659,588 A | * 5/1972 | Kahn et al. | 128/2 R |
| 3,911,902 A | * 10/1975 | Delpy | 128/2.05 D |
| 3,942,382 A | * 3/1976 | Hök | 73/398 |
| 4,476,880 A | 10/1984 | Giem et al. | |
| 4,817,624 A | * 4/1989 | Newbower | 128/692 |
| 4,873,990 A | 10/1989 | Holmes et al. | |
| 5,683,345 A | * 11/1997 | Waksman et al. | 600/3 |

FOREIGN PATENT DOCUMENTS

| | | |
|---|---|---|
| DE | 2117541 | 10/1972 |
| DE | 3011266 | 3/1980 |
| DE | 3933827 | 10/1989 |
| EP | 0632992 | 1/1995 |

OTHER PUBLICATIONS

Smith et al. *Sensors: Sensor Design and Packaging.* vol. 1, 79–106. VCH Verlagsgesellschaft, Weinheim. (1989).
Elektronik Notizen. *Pressure Distribution Can Be Measured Capacitively.* No. 12, p. 11. (1979).

* cited by examiner

Primary Examiner—Kevin Shaver
Assistant Examiner—Patricia Mallari

(57) ABSTRACT

The invention relates to a sensor system for measuring pressure profiles. Such systems can be used wherever pressure distributions in one or two dimensions are to be measured. An important field of application is medicine. Here pressure profile measurements, e.g. in urology, proctology, cardiology and other disciplines can be carried out with the aid of catheters. The measuring catheter is formed as a tubular flexible hollow body (1) of length L. An outer pressure load p(x) is represented on tube (1) as a cross-sectional function A(x). The local cross-section A(x) is scanned by the tube being filled from one side at (x=0) continuously with a liquid substance (I) which displaces substance (II) to the filling length $X_A$. The filling length $x_A$ can be measured according to differing methods: measurement of the electrical resistance, measurement of the electrical capacity, measurement of acoustic resonance.

32 Claims, 12 Drawing Sheets

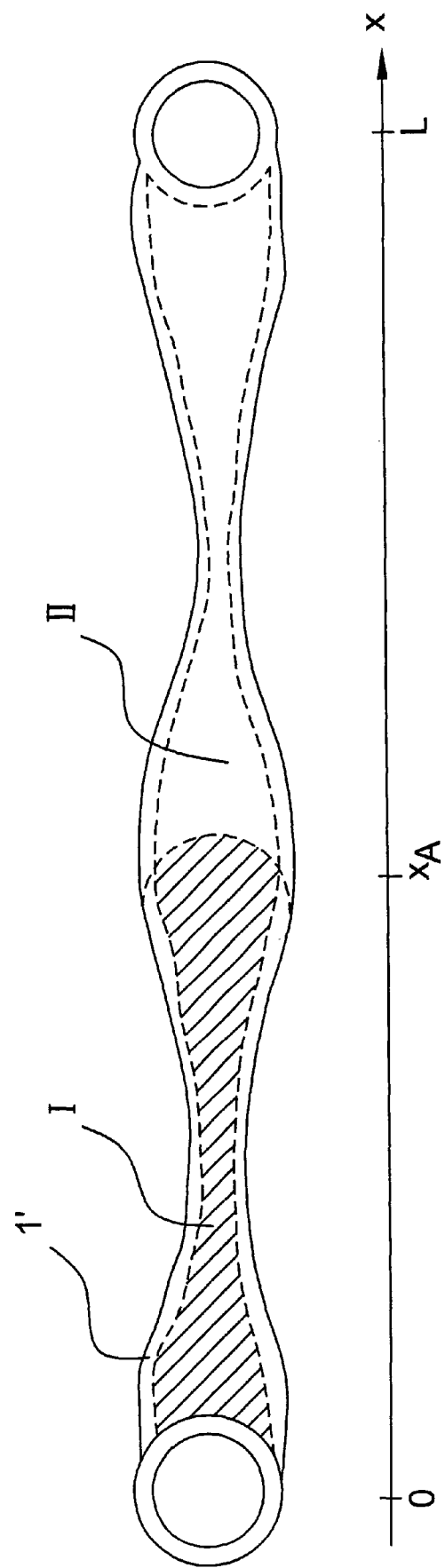

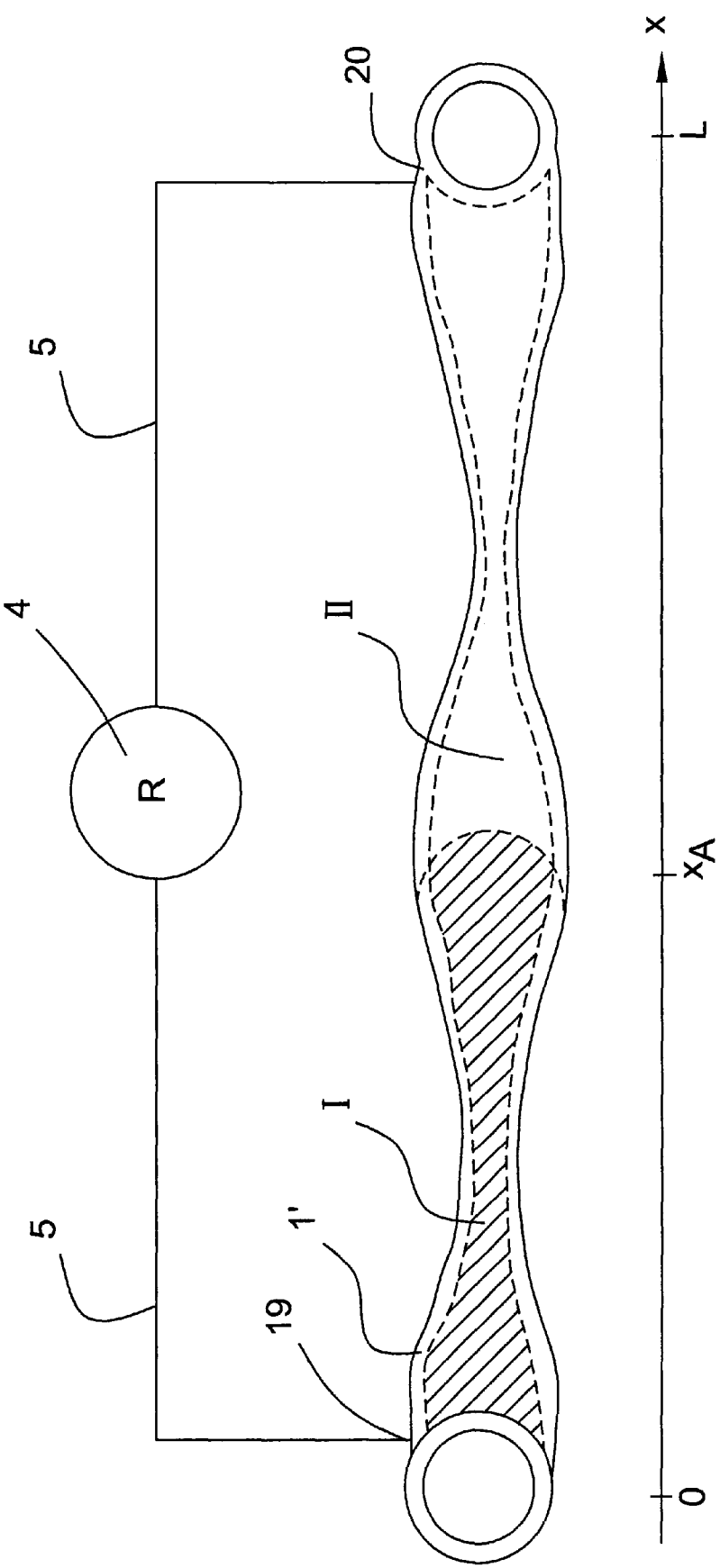

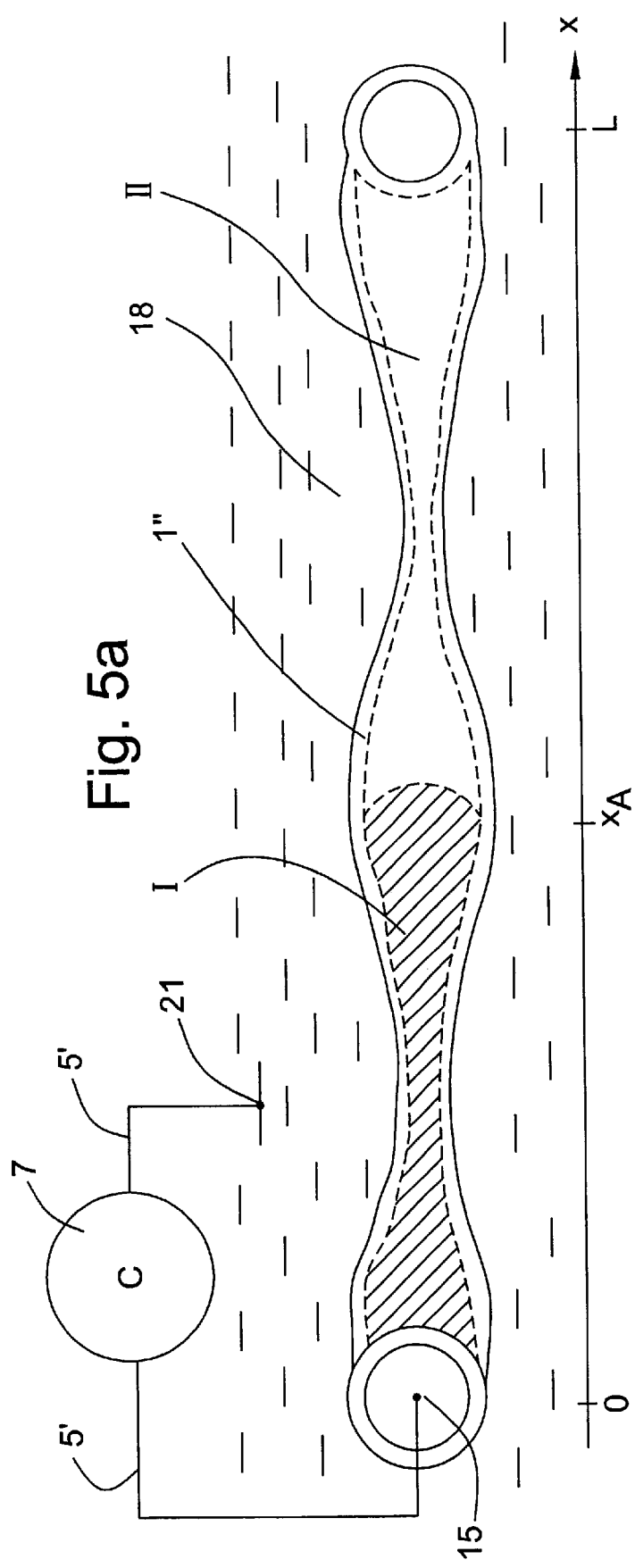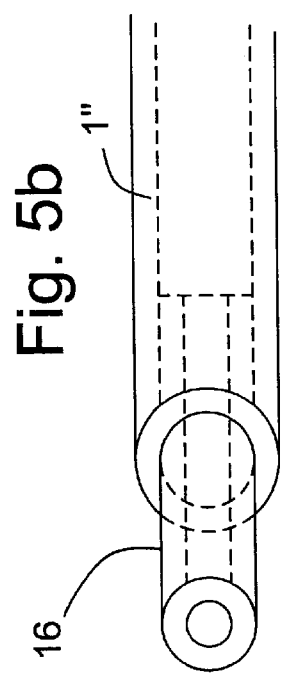

SENSOR SYSTEM FOR MEASURING PRESSURE PROFILES

The invention relates to a sensor system for measuring pressure profiles. Such systems can be used wherever pressure distributions in one or two dimensions are to be measured. An important field of application is medicine. Here pressure profiles can be measured for example in urology, proctology cardiology and other disciplines, with the aid of catheters.

It is known that sensors are used to measure pressure. Such sensors are so small that they can be fitted for example into a catheter (cf. e.g.: R. L. Smith, S. D. Collins: Sensor Design and Packaging in W. Göpel, J. Hesse, J. N. Zemel: Sensors, Volume 1, VCH Verlagsgesellschaft, Weinheim, 1989, pages 79–106).

What is disadvantageous about such sensors is that pressure can only be measured in one place with their help. In order to record pressure profiles, pressure sensor arrays would have to be used, or the sensor would have to be moved during the measurement process.

Sensor arrays are technically complicated and expensive; the movement of sensors is difficult to carry out in many applications, or even impossible.

Therefore, the object underlying the invention is to realise a measurement system in which a pressure profile can be measured, without the catheter having to be moved during this process. The use of expensive sensor arrays is intended here to be dispensed with.

Figure 1A:
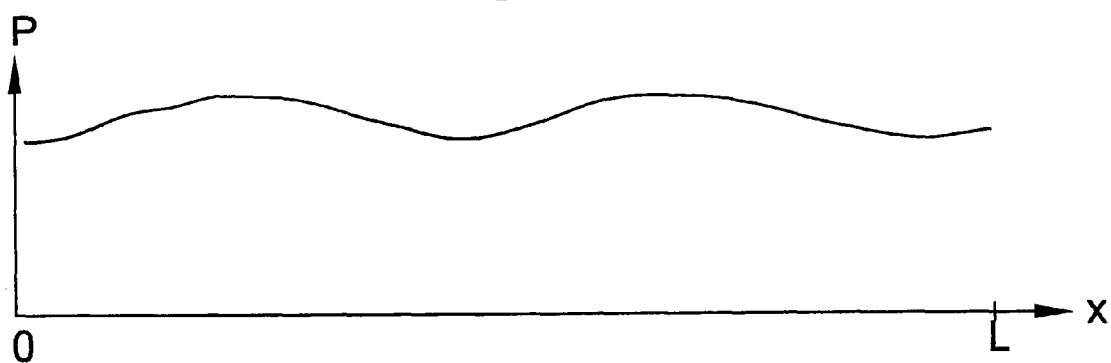
Figure 1B:
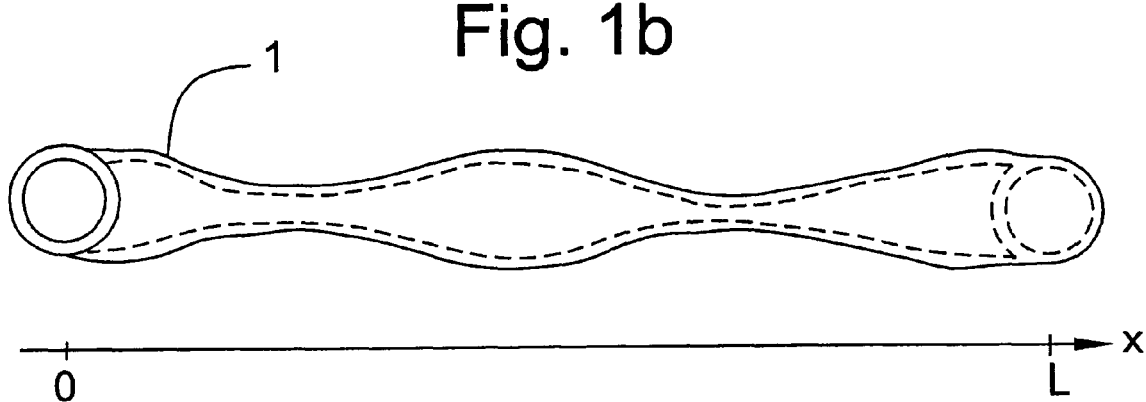
Figure 1C:
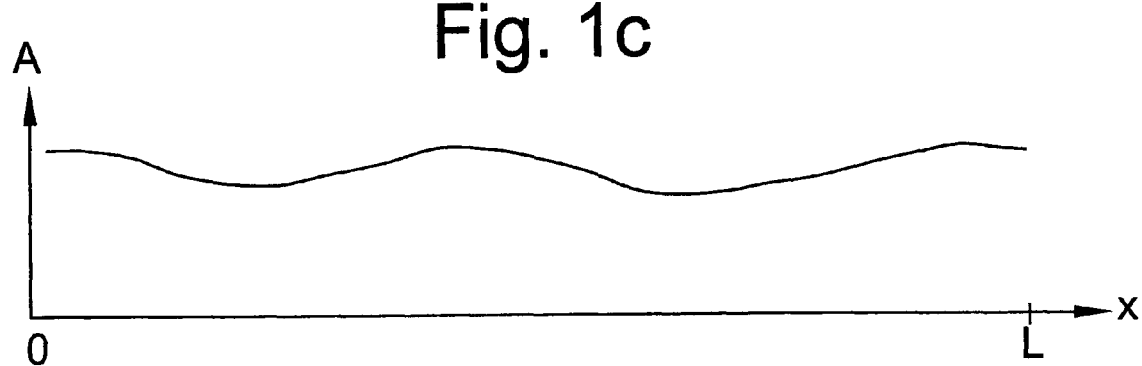

This object is achieved according to the invention in that the measurement catheter is formed as a tubular flexible hollow body (1) of length L—called "tube" below—(FIG. 1b). The tube has an inner circular, oval, rectangular or other shaped cross-section of size A. An external pressure load p(x) (FIG. 1a) is represented on the tube (1) as a cross-sectional function A(x) (FIG. 1c). This comes about by compression of the tube (1), which is caused by the difference between external and internal pressure.

The correlation between the external pressure load p(x) and the cross-sectional function A(x) can be varied in the sense of a measurement range adjustment through alteration of the pre-set pressure $p_o$ in the interior of the tube (1).

The local cross-section A(x) is scanned by the tube being filled continuously from one side (x=0) with a liquid substance (I) which displaces substance (II) up to filling length $x_A$ (FIG. 2).

For the correlation between the filling length $x_A$ and the filling volume $V_f$ the following is true:

$$dx_A = dV_f / A(x_A)$$

From this follows the filling volume $V_f$ (substance I):

$$V_f = \int_{x=0}^{x=x_A} A(x)dx$$

The filling length $x_A$ can be measured according to different methods:
measurement of the electrical resistance
measurement of the electrical capacity
measurement of the acoustic resonance.

The filling length $x_A$ can be ascertained in a simple manner through measurement of the electrical resistance with the aid of a measuring instrument (4).

In one of the possible measuring methods, the measuring instrument (4) is connected via the electrical supply lines (5) with the tube (1') (FIG. 3). The measurement can be taken with direct current or alternating current at electrical voltages of U>10 mV.

The tube (1') of length L has an electrical resistance in the range between $10^2 – 10^7$ Ω. This is achieved by the tube (1') being manufactured from electrically conductive plastics material, or by the inner surface being coated with an electrically conductive film.

To fill the tube (1'), a substance (I) with a specific resistance $\rho_1$ is used. The displaced substance (II) has a specific resistance $\rho_2$. The following must be true:

$$\rho_2 \gg \rho_1$$

Substance (I) can be any kind of electrically conductive liquid (e.g. salt solution: NaCl, KCl . . . ) Substance (II) can be air, some other gas, but also a liquid (e.g. oil) which fulfills the condition $\rho_2 \gg \rho_1$.

If, per length unit along the tube, the resistance of substance (I) is very much lower than the resistance of the tube, in the region filled with substance (I), the electrical resistance of the tube is approximately short-circuited.

As the tube is filled, therefore, there arises a measurable electrical resistance R as a function of the filling volume. Since the filling length $x_A$ increases more quickly in the region of smaller cross-sections A than in regions of greater cross-sections, in the course of function R ($V_f$) larger amounts of increase occur in the regions with small cross-sections. The differential quotient $dR/dV_f$ is thus a representation of the cross-sectional function A ($X_A$):

$$\frac{dR}{dV_f} = \left(-\frac{1}{A(x_A)}\right)$$

For the measurable resistance R, the following statement arises:

$$R = \frac{R_f}{L} \cdot x_A + \frac{R_s}{L}(L - x_A)$$

In this, $R_f$ is the electrical resistance of the filled tube, $R_s$ is the resistance of the empty tube and L is the tube length.

For $R_f \ll R_s$, for the course of the electrical resistance, R arises as a function of the filling length $x_A$ $$\frac{R}{R_s} \approx -\frac{1}{L}x_A + 1$$

and from this for $x_A$ $$x_A \approx L\left(1 - \frac{R}{R_s}\right)$$

The course of the pressure profile p(x) is represented by the amount of the differential quotient $dR/dV_f$ over the filling length $x_A$.

Figure 4A:
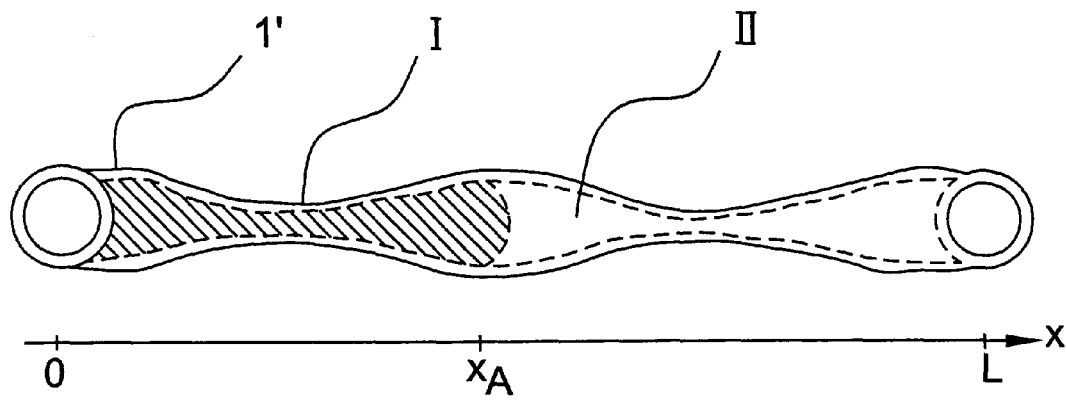
Figure 4B:
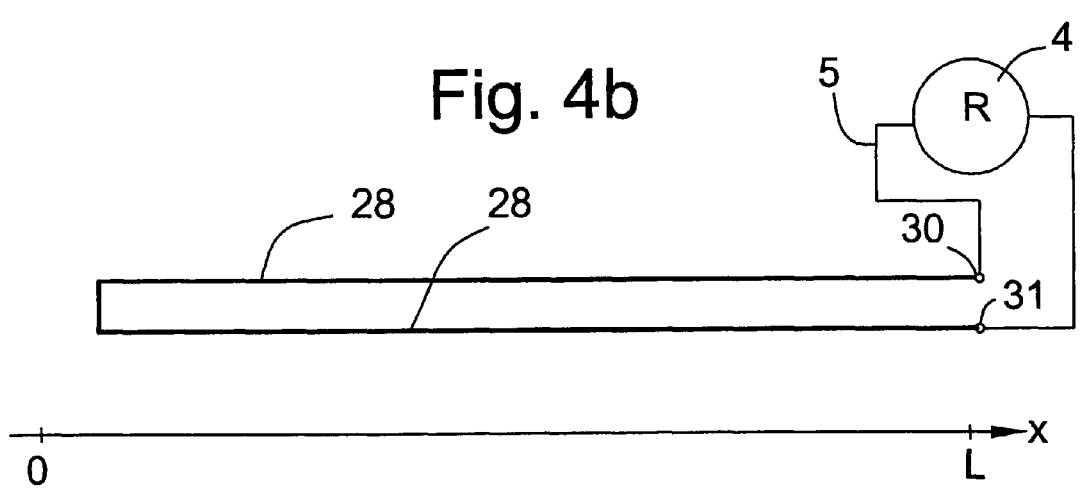

A similar measuring principle arises if the tube (1) has a very high electrical resistance $R_{so}$. Into the inner cavity of the tube (1) (FIG. 4a) is inserted an electrical conductor (28) (e.g. resistance wire) with an electrical resistance $R_{sd}$ (FIGS. 4b+c). For the resistances $R_{so}$ and $R_{sd}$ the following should apply $R_{sd} < R_{so}$.

The electrical conductor (28) can be inserted e.g. in the form of a loop (e.g. wire loop) (FIG. 4b).

When the tube (1) is filled with a substance (I), which, in comparison with the electrical conductor (28), has a low specific resistance, the resistance portion of the electrical conductor (28) between x=0 and x=$x_A$ is approximately short-circuited. Analogously to the above represented example, the following arises for the electrical resistance between the connection points (30) and (31) which is measurable with the resistance measuring instrument (4):

$$\frac{dR}{dV_f} - \left(-\frac{1}{A(x_A)}\right)$$

The pressure profile can be measured in the manner already described.

It is also possible to insert just one electrical conductor (28') (e.g. resistance wire) into the inner cavity of the tube (1). The circuit is closed with the aid of a low-impedance electrical conductor (29) (e.g. wire) which can be realised with or without external electrical insulation.

The pressure profile can also be measured on the basis of a capacity measurement. For this purpose, the tube (1") is manufactured from an electrically insulating material (FIG. 5a). The capacity can be measured with the aid of a capacity measuring instrument (7) between the electrically conductive filling (I) and an electrically conductive medium (18), which surrounds the tube (1").

The measurable capacity C increases as a function of the filling length $x_A$.

FIG. 5b shows the possible way of providing contact for substance (I) with the aid of a short pipe (16) which is inserted into the end of tube (1").

Figure 6:
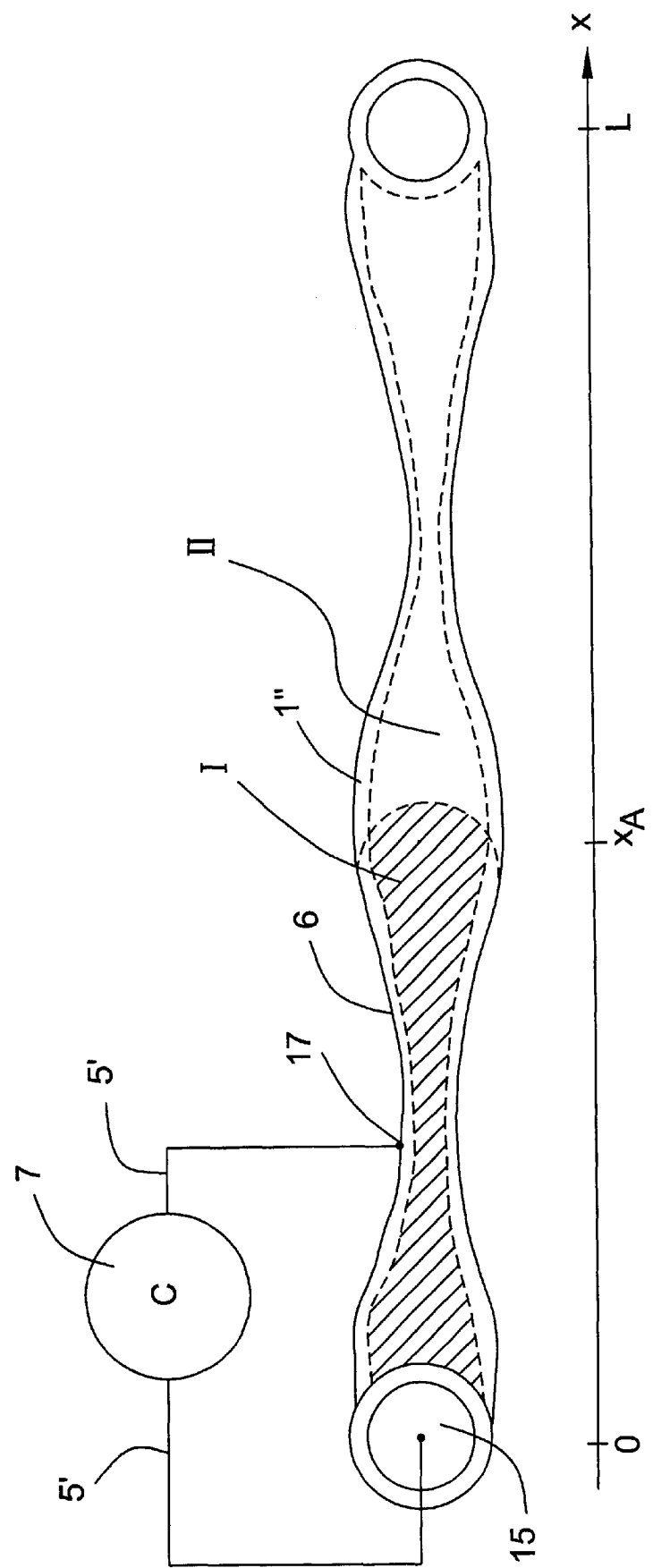

It is also possible to measure the capacity between the electrically conductive substance (I) and an electrically conductive coating (6), which is located on the surface of the tubular flexible hollow body (1") (FIG. 6).

For the measurable capacity C the following arises:

$$C = c_f x_A / L$$

Here $c_f$ is the capacity of the filled tube.

$x_A$ arises as $x_A = L\, C/C_f$

The differential quotient $dC/dV_f$ is the representation of the pressure profile over the filling length $x_A$.

The filling length $x_A$ can also be detected by an acoustic method. If air or some other gas is used as substance (II), through acoustic excitation of this gas column the unfilled length ($L-x_A$) of the tube (1) can be measured by determining the resonance frequency.

The advantages achieved with the invention lie in particular in the fact that pressure profiles can be measured without the measuring catheter having to be machine-operated. In addition to this it is possible, through periodic enlargement or reduction of the filling height $x_A$ to scan specific regions. Through variation of the counter pressure, information can be obtained about the solidity of the material exercising pressure.

Embodiments of the invention are represented in the drawing and are explained more fully in the following description.

Different embodiments of the invention are represented in FIGS. 3 to 9. The figures show:

FIG. 1: a) an external pressure load as a function of the path;
b) a measuring catheter in the form of a tube under the pressure load;
c) the cross-sectional function of the measuring catheters when pressure is applied.

FIG. 2: a measuring catheter filled with different substances.

FIG. 3: measuring principle on the basis of a resistance measurement.

FIG. 4: measuring principle variations on the basis of a resistance measurement.

FIG. 5: a) measuring principle on the basis of a capacity measurement
b) provision of electrical contact for substance (I)

FIG. 6: measuring principle according to FIG. 5 with an additional electrically conductive layer (6).

Figure 7:
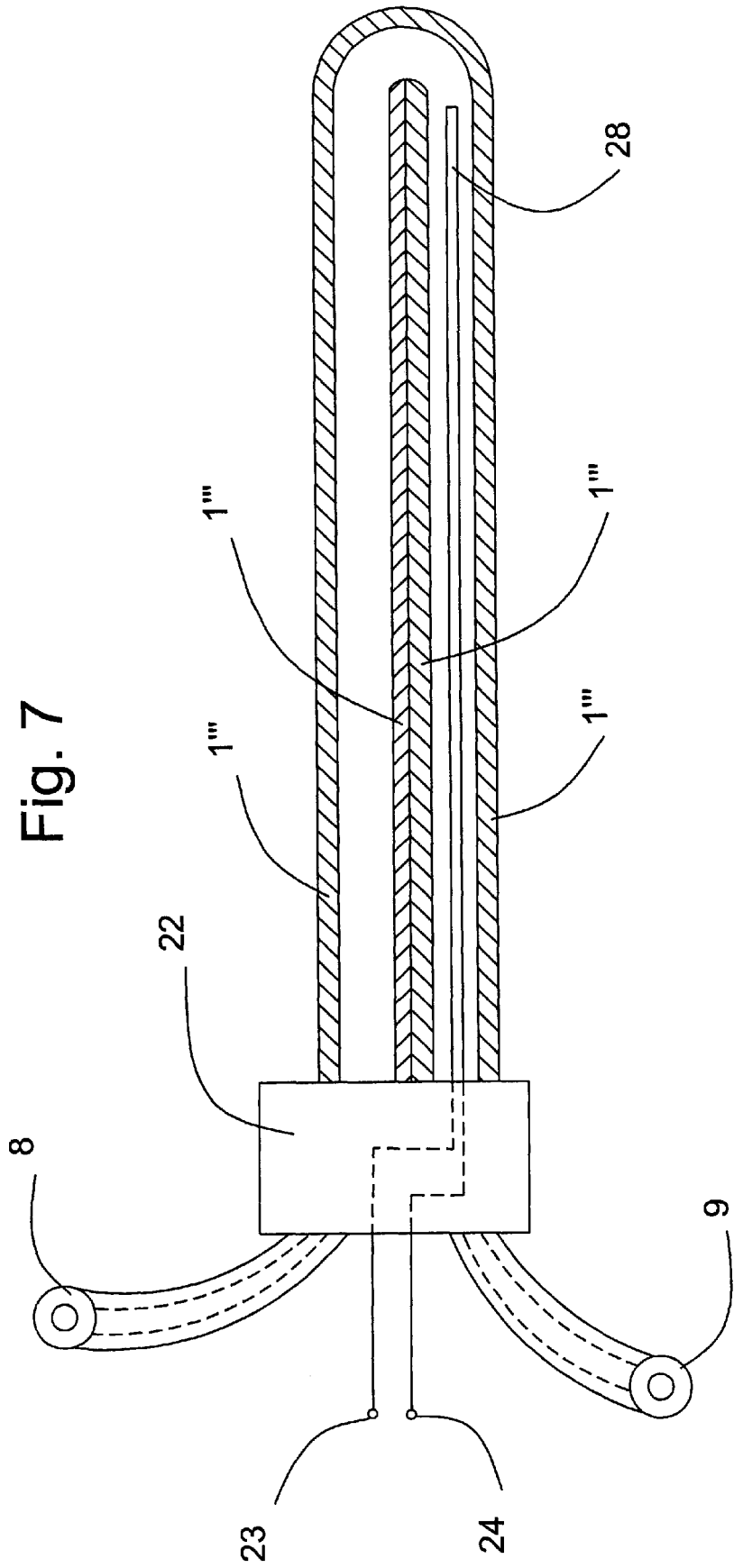

FIG. 7: design of a measuring catheter with a double cavity.

Figure 8:
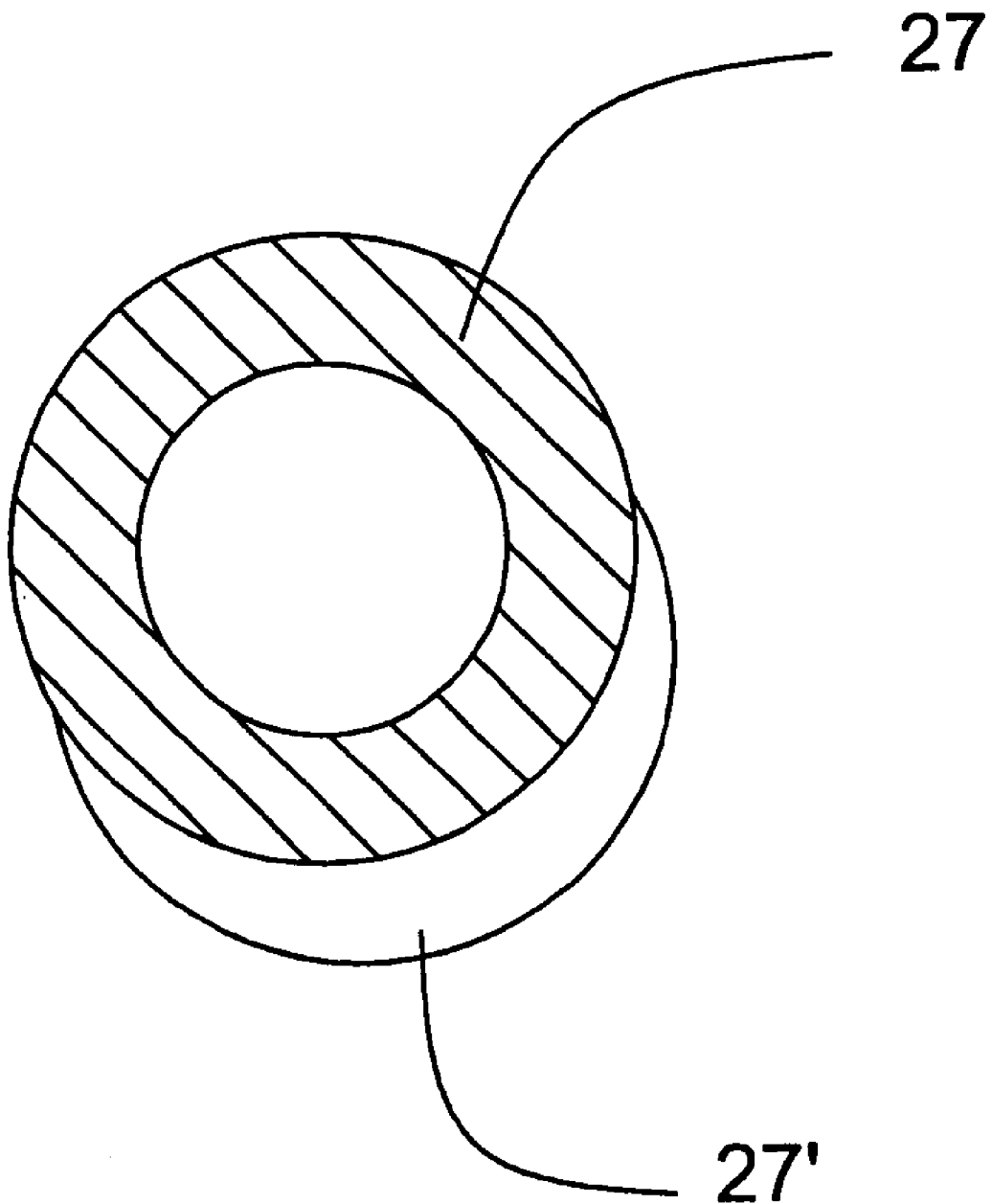

FIG. 8: measuring catheter with unsymmetrical wall reinforcement.

Figure 9:
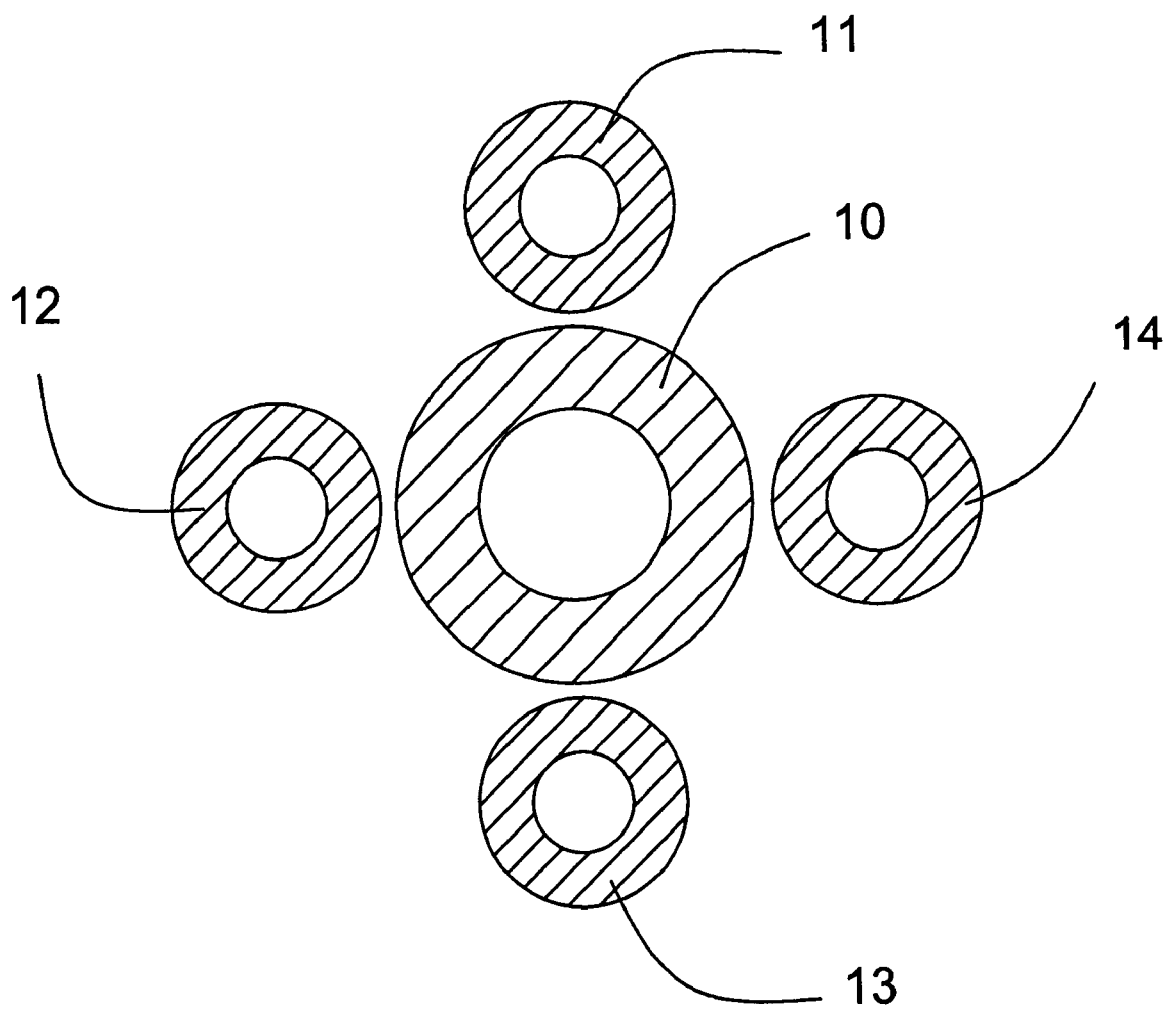

FIG. 9: measuring catheter with four measuring tubes offset by 90°.

Figure 10:
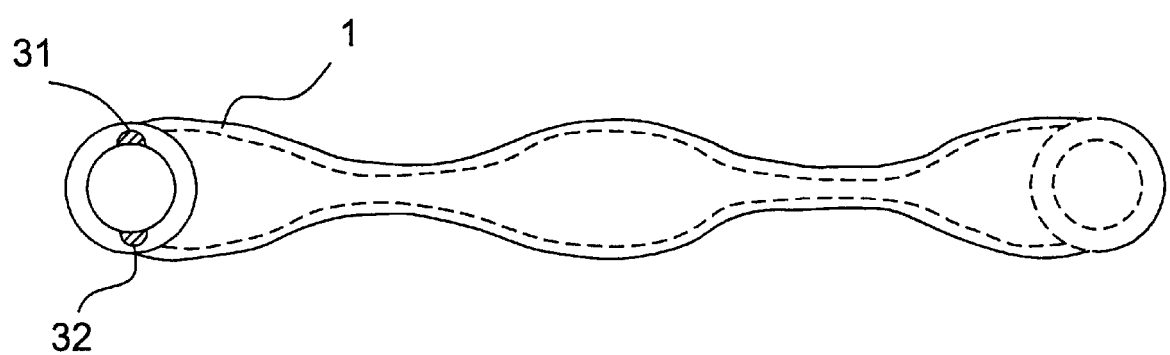

FIG. 10: a view of a further embodiment of a tube.

Figure 11A:
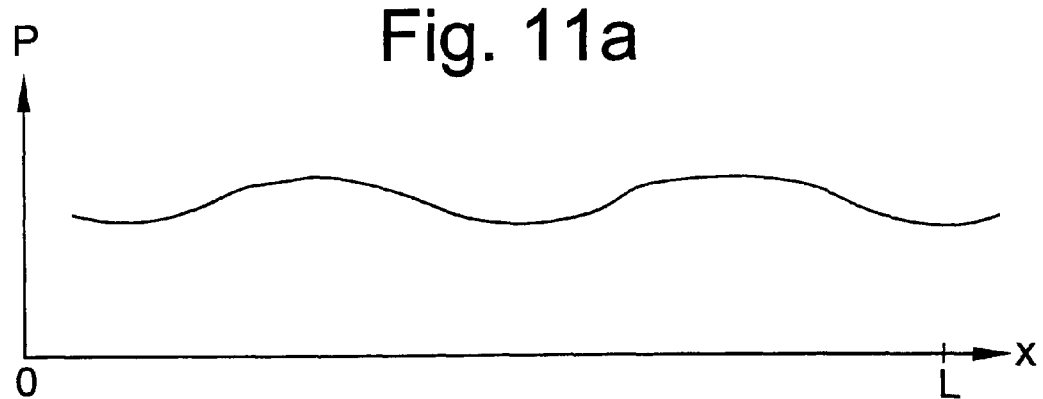
Figure 11B:
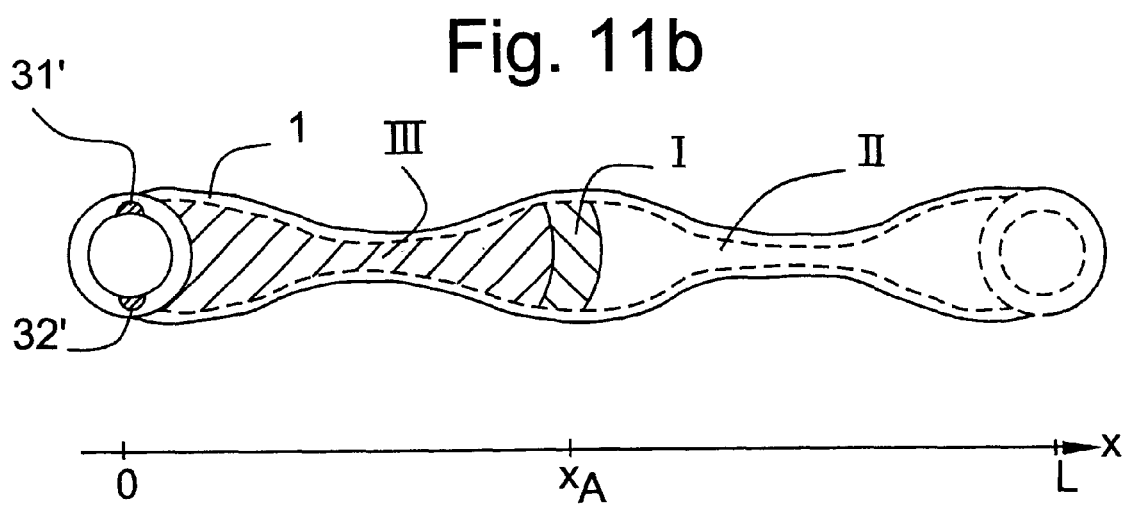
Figure 11C:
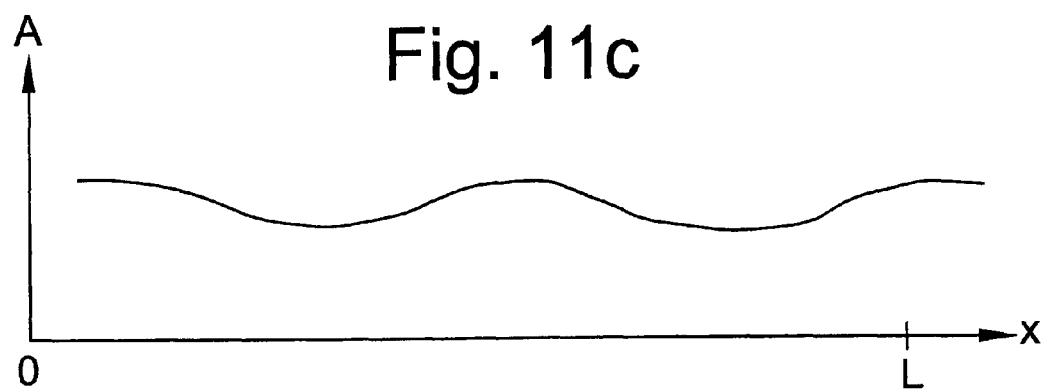

FIG. 11: a further embodiment of a further measuring principle.

Figure 12A:
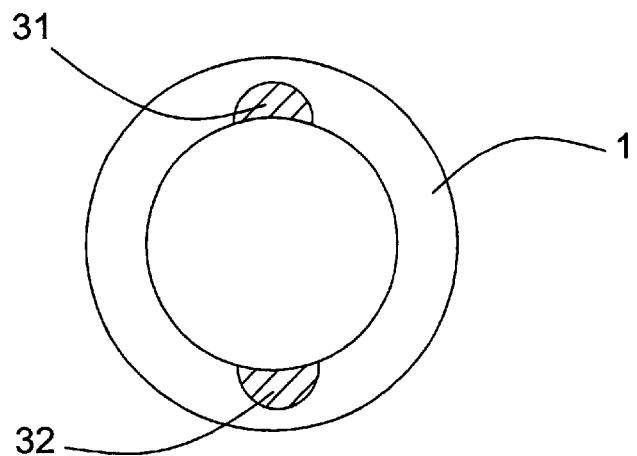
Figure 12B:
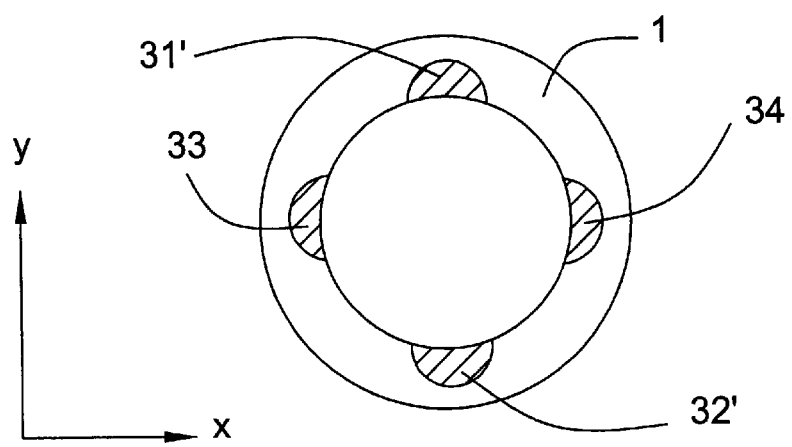

FIG. 12: arrangements of conductor tracks in the tube for the multi-dimensional measurement of the pressure profile.

FIG. 3 shows an embodiment of the invention which works on the basis of measuring electrical resistance. The tube (1') is manufactured e.g. from silicon, rubber, latex, polyurethane, PVC, PP, PE, Pa, PUR or some other material.

Such plastics materials can be made electrically conductive through doping with carbon or metal powder.

The electrical resistance of the tube with length L is about $10^6$ Ω. Length L is 1 cm–10 m, preferably 1 m. The tube has an external diameter of between 1 mm and 10 cm preferably in the range between 2 mm and 5 mm. The tube wall thickness is between 0.1 mm and 5 mm, preferably in the range between 0.2 mm and 1 mm.

A resistance measuring instrument (4) is connected via the electrical supply lines (5) to the tube (1'). Contact is provided e.g. with the aid of conductive silver or conductive glue at points (19) and (20).

With the aid of a pump, the tube (1') is filled continuously at point x=0 with substance (I) (e.g. monomolecular KCl solution with a specific conductance of approximately 0.1 S/cm or NaCl solution . . . ) and the resistance R is measured as a function of the filling volume $V_f$. The pressure profile is determined as portrayed above.

In another embodiment (not represented) the tube (1) is manufactured from an electrically insulating material. The inner tube surface is coated with an electrically conductive layer, which, as in the preceding example, is connected via the electrical supply lines (5) to the resistance measuring instrument (4).

In a further embodiment, a resistance wire loop (FIG. 4b) (e.g. made of constantan) with an electrical resistance of $10^6$ Ω is inserted into the inner cavity of the electrically insulating tube (1). This wire is connected via connection points (30) and (31) and the electrical supply lines (5) to the resistance measuring instrument (4).

Figure 4C:
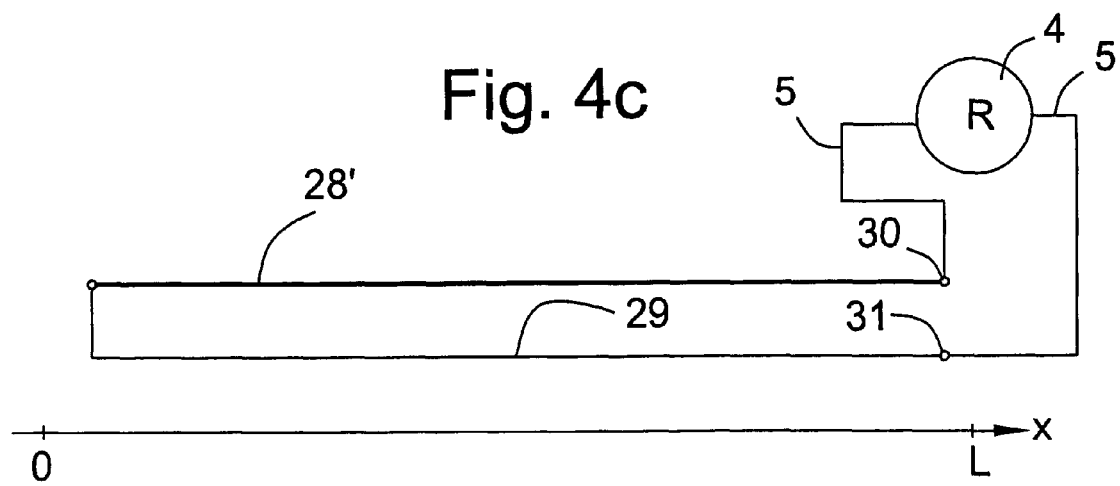

In FIG. 4c, the electrical conductor (28'), is connected to a low-impedance and externally electrically insulated conductor (29) (e.g. wire) and via connection points (30) and (31) and the electrical supply lines to the resistance measuring instrument (4).

It is just as possible to wind the electrical conductor (28') spirally around the electrical conductor (29) (no figure).

The electrical conductors (28, 28', 29) can be applied on any electrically insulating and flexible support material according to prior art, in thick-film or thin-film technology, and the flexible support material inserted into the inner cavity of the tube (1).

A further embodiment is represented in FIG. 10. It shows, on the basis of FIG. 4, an electrically insulating tube (1) which consists e.g. of silicon, and into which, by co-extrusion of electrically conductive silicon, two resistance tracks (31, 32) with the same or different resistance values, have been inserted along the whole length of the tube.

What is crucial is that the resistance value of at least one resistance track (31 or 32) per length unit is considerably greater (e.g. at least 10 kΩ) than the resistance value of substance I (e.g. 300 Ω) per length unit.

If the resistance tracks (31 and 32) at the right-hand end of the tube (1) are connected to a resistance measuring instrument, as described in FIG. 4, pressure profiles can be measured.

FIG. 5 shows a further embodiment of the invention. The pressure profile is here measured on the basis of a capacity measurement with the aid of a capacity measuring instrument (7). The electrical capacity is measured between the electrically conductive substance (I) and an electrically conductive medium (18) which surrounds the tube (1"). The tube (1") is manufactured e.g. from electrically insulating PU material which acts as a dielectric of the electrical capacity. The medium (18) can be a common salt solution, to which contact is provided with the aid of a metal electrode (21) (e.g. made of gold, silver or carbon). Providing contact to the substance (I) in the interior of tube (1) at point (15) is represented schematically in FIG. 5a. A possible way of realising this electrical contact is shown in FIG. 5b. At the end of tube (1") is inserted a short metal pipe (16), which, when the tube (1") is filled, comes into contact with substance (I). The pipe (16) is connected via the electrical supply line (5') to the capacity measuring instrument (7).

The pressure profile is measured in the manner represented above.

If the pressure profile has been determined on the basis of a capacity measurement but not in an electrically conductive medium (18), in another embodiment (FIG. 6) the capacity between substance (I) and an electrically conductive layer (6), which is located on the external surface of the electrically insulating tube (1"), can be measured.

This layer (6) consists e.g. of carbon, conductive lacquer or a thin metal film. It is applied over the whole surface or realised over the length of the tube in strips.

Films of this kind can be sprayed on, or applied by a dipping process or a vapour-deposition process in a vacuum.

Layer (6) is connected e.g. at point (17) by means of conductive silver to the electrical supply line (5') of the capacity measuring instrument (7).

An embodiment of a measuring catheter having a double cavity is represented in FIG. 7. Here (1''') is the flexible tube (with a double cavity). The length of the tube between its tip (on the right in FIG. 7) and the terminal block (22) is 1 m. The external diameter of the double-cavity tube (1''') is 4 mm, the wall thickness 0.3 mm. The double-cavity tube (1''') is connected via terminal block (22) with tubes (8) and (9), via which tubes substances (I) and (II) are supplied or led away.

The measurement profile is measured in an analogous way to FIG. 4b by means of a loop made of resistance wire (28). For the measurement, a resistance measuring instrument is connected via connection points (23) and (24).

To measure the pressure profile, as substance (I) e.g. monomolecular common salt solution is supplied via tube (8) with the aid of an external pump. The air or any other gas can escape from tube (1''') via tube (9). A pressure sensor or an adjustable valve can be connected to tube (9). With the aid of the sensor and the valve, it is possible to control the inner pressure in tube (1'''). The difference between the pressures outside and inside the tube (1''') determines the evaluable pressure measurement range.

In FIG. 8, a single-cavity tube for pressure profile measurement is represented in cross-section. The unsymmetrical construction of the wall makes possible a cross-sectional alteration even when there is a pressure difference between internal and external pressure occurring evenly radially. The wall regions (27) and (27') can be manufactured from differing materials. For wall (27) a flexible material is preferably used, and for wall (27') a more rigid material.

FIG. 9 shows a measuring catheter with four measuring tubes offset by 90°. With the aid of the measuring tubes (11, 12, 13 and 14), the pressure profile is measured as represented above, and substances (I) or (II) are returned via tube (10). Resistance wire arrangements as per FIGS. 4a and b can be inserted into the measuring tubes (11 to 14).

In the preceding embodiments, measurement arrangement for one-dimensional pressure profile measurement were quoted. It is also possible to measure two-dimensional pressure distributions. For this purpose, a plurality of tubes (1) is arranged in parallel (no figure). Substances (I) and (II) can be supplied or led away by means of all the parallel tubes (1) being filled in succession. They are thus arranged serially in relation to being filled.

Each of the tubes (1) can be equipped with an arrangement as per FIG. 4b or 4c. The different electrical conductors (28) are led to measuring electronics via connection points (30) and (31).

A measuring catheter can also have additional cavities which are free for other purposes.

FIG. 11 shows an additional embodiment of the invention. Here two conductor tracks (31', 32') are introduced into a silicon tube by co-extrusion. These conductor tracks are to be realised with as low-impedance as possible. To measure pressure profiles, from the left-hand end of the tube (1) a substance I is filled, which only takes up a small partial volume of the tube and displaces substance II.

In contrast to all the preceding embodiments, a substance III is now introduced into the inner tube volume. Substances II and III consist e.g. of oil, air or any other liquid or gaseous substance which has a very high specific resistance. Substance I is, on the other hand, a liquid with a low specific resistance (e.g. common salt solution).

Electrical connection between the conductor tracks (31'and 32') can thus only be provided via the partial volume of the tube filled with substance I. An alteration in the cross-section of the tube, caused by an external pressure, causes a reduction in the distance between the conductor tracks (31' and 32'). This leads, in the region of the partial volume of substance I, to a measurable alteration in the electrical resistance or electrical capacity.

In this embodiment, the pressure profile can be scanned as in the preceding examples. However, a differential quotient does not have to be formed here since the measurable alteration in resistance is directly proportional to the alteration in pressure.

In addition, with this embodiment it is possible, with a constant filling length $x_A$ to measure the pressure at location $X_A$ as a function p(t) of time.

Here an alternative method can be employed to determine the filling length $x_A$, if the conductor tracks 31' and 32' have differing resistances per length unit. The measurable electrical resistance between the left-hand end of resistance track 31' and the right-hand end of resistance track 32' or the left-hand end of resistance track 32' and the right-hand end of resistance track 31' is dependent on the filling length $x_A$ and can thus be used for the measurement.

Further embodiments are shown in FIG. 12. FIG. 12 shows in cross-section the tubular hollow body. In FIG. 12a is shown tube 1 with the resistance tracks (31 and 32) as was described in the embodiment according to FIG. 10.

Figure 12C:
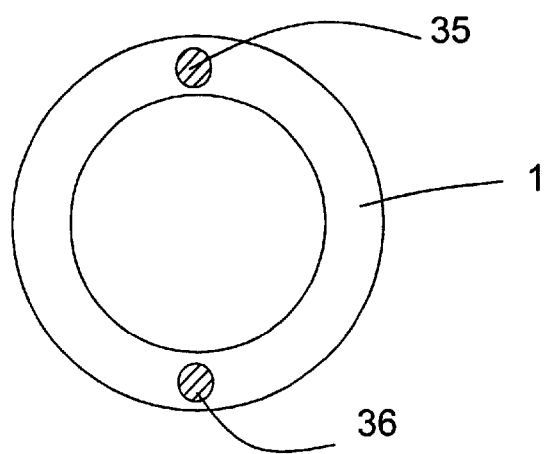

It is also possible to analyse pressure alterations on the tube (1) according to the X or Y component. For this purpose, two resistance tracks (31' and 32') plus two additional resistance tracks (33 and 34) are introduced into the same tube (1). Resistance measurements on the pair of resistance tracks (31' and 32') analyse a pressure component in the Y direction, whilst the X component is measured on resistance pair (33 and 34). For capacity measurements, conductor tracks (35 and 36) in the tube (1) may be used (FIG. 12c). The pressure can be measured as a function of the location and as a function of time on the basis of the embodiment according to FIG. 11, in that the resistance measurement is measured by a capacity measurement on the conductor tracks (35 and 36). Since substances II and III have a negligible electrical conductivity, only the partial volume of the tube (1), which is filled with substance I, contributes to the capacity measurement.

What is claimed is:

1. A sensor system for measuring pressure profiles comprising a measuring catheter formed as a tubular flexible hollow body of length L and filled with a substance (II); means for filling, continuously or in sections, the hollow body filled with substance (II) from one side with a liquid substance (I) which displaces substance (II) to a filling length $X_A$ substance (II) being a gas or having a different specific resistance from substance (I); and means for scanning a local cross-sectional function A(x) of the tubular flexible hollow body, which represents the external pressure p(x) applied to the hollow body, by continuously measuring the filling length $X_A$ during filling of the hollow body with substance (II) and determining the cross sectional function A(x) according to $$dx_A = dV_f / A(x_A)$$

wherein $V_f$ represents the filling volume of substance (I).

2. The sensor system according to claim 1, wherein the correlation between the external pressure load p(x) and the cross-sectional function A(x) is varied in order to adjust the measurement range of the external pressure load p(x) by alteration of the external pressure load p(x) by alteration of the pressure p of substance (II) in the interior of the hollow body.

3. The sensor system according to claim 1, wherein the sensor system includes means for detecting the filling length $X_A$ by measuring the electrical resistance and/or the electrical capacity, it being possible to fill the hollow body first in a small section with substance (I), in such a way that it displaces substance (II) to filling length $x_A$, and in addition means for filling the hollow body with a substance (III) in such a way that it follows directly onto substance (I) in the interior of the hollow body volume, substances (II) and (III) having very high specific resistances and substance (I) a very low specific resistance, and the means for detecting the filling length $x_A$ having a resistance measuring instrument and/or capacity measuring instrument which is connected to conductor tracks disposed opposite to each other along the tube on or in the tube, and which detects alterations in pressure as alterations in electrical resistance or electrical capacity between the two conductor tracks.

4. The sensor system according to claim 1, wherein the sensor system includes means for detecting the filling length $x_A$ by measuring the electrical resistance, the hollow body having an electrical resistance in the range between $10^2$ and $10^7$ Ω, substance (I) a specific resistance $_1$ and substance (II) a specific resistance $_2$ with $_2 \gg _1$, and the course of the pressure profile (x) being represented by the amount of the differential quotient $dR/dV_f$ over the filling length $x_A$ $$x_A \approx L\left(1 - \frac{R}{R_s}\right)$$

$R_s$ representing the electrical resistance of the empty hollow body, R the electrical resistance of the hollow body filled to $x_A$ and $V_f$ the filling volume with substance (I).

5. The sensor system according to claim 1, wherein the hollow body is manufactured from electrically conductive plastics material, or the inner surface of the hollow body is coated with an electrically conductive film.

6. The sensor system according to claim 1, wherein the hollow body consists of an electrically insulating material, and an electrically conductive layer is applied to the inner surface of the hollow body, which layer is connected via electrical supply lines to a resistance measuring instrument.

7. The sensor system according to claim 1, wherein the hollow body consists of electrically insulating material and in its inner cavity is inserted a resistance wire loop, with an electrical resistance of $10^6$ Ω, and this wire is connected via two connection points to a resistance measuring instrument.

8. The sensor system according to claim 1, wherein substance (I) is an electrically conductive liquid, substance (II) and/or substance (III) is air, some other gas, or a liquid the specific resistance $_{s2}$ of substance II and/or the specific resistance $_{s3}$ of substance III with the specific resistance $_{s1}$ of the first substance fulfilling the condition $_{s2} \gg _{s1}$ and/or $_{s3} \gg _{s1}$.

9. The sensor system according to claim 1, wherein the hollow body has a very high electrical resistance $R_{so}$, and an electrical conductor with an electrical resistance $R_{sd}$ is inserted into the inner cavity of the hollow body, the condition $R_{sd} < R_{so}$ being valid for resistances $R_{so}$ and $R_{sd}$.

10. The sensor system according to claim 9, wherein the electrical conductor is inserted in the form of a loop into the inner cavity of the hollow body.

11. The sensor system according to claim 1, wherein an electrical conductor is arranged in the inner cavity of the hollow body, and a low-impedance electrical conductor, with or without external electrical insulation, is provided to close the circuit.

12. The sensor system according to claim 1, wherein at least two resistance tracks with identical or differing resistance values are disposed over the length of the hollow body on its internal circumference, a resistance measuring instrument being connected to two adjacent ends of the two resistance tracks and wherein the resistance value of at least one resistance track per length unit is significantly greater than the resistance value of substance (I).

13. The sensor system according to claim 1, wherein substance (I) is electrically conductive, the hollow body is manufactured from an electrically insulating material, and the means for scanning a local cross-sectional function A(x) have means for determining the capacity between the electrically conductive substance (I) and an electrically conductive medium, which surrounds the tube.

14. The sensor system according to claim 1, wherein an electrically conductive coating is applied to the surface of the tubular flexible hollow body, wherein substance (I) is electrically conductive and the means for scanning a local cross-sectional function A(x) have means for determining the capacity between the coating and substance (I), the differential quotient $dC/dV_f$ being a representation of the pressure profile over the filling length $x_A$, wherein C represents the determined capacity and $V_f$ the filling volume with substance (I).

15. The sensor system according to claim 14, wherein the electrically conductive layer on the external surface of the electrically insulating hollow body is selected from the group consisting of carbon, conductive lacquer and a thin metal film.

16. The sensor system according to claim 14, wherein the electrically conductive layer is attached to the external surface of the electrically conductive hollow body on the whole surface of the hollow body, or is disposed in strips over the length of the hollow body.

17. The sensor system according to claim 1, wherein the means for scanning a local cross-sectional function A(x) have means for detecting the filling length $x_A$ in an acoustic manner, substance (II) being air or some other gas, and by acoustic excitation of this gas column, the non-filled length $(L-x_A)$ of the hollow body may be determined by determining the resonance frequency.

18. The sensor system according to claim 1, wherein the hollow body contains silicon, rubber, latex, polyurethane, polyvinyl chloride (PVC), polypropylene (PP), polyethylene (PE), Pa or PUR.

19. The sensor system according to claim 1, wherein the hollow body contains plastics material which is made electrically conductive by doping with carbon or metal powder, the electrical resistance of the hollow body is $10^6$ Ω, length L of the hollow body is 1 cm to 10 m, the hollow body has an external diameter of between 1 mm and 10 cm, and/or the wall thickness of the hollow body is between 0.1 mm and 5 mm.

20. The sensor system according to claim 1, wherein the means for filling continuously or in sections have a pump for filling the hollow body continuously at location x=0 with substance (I), and wherein the resistance R may be measured as a function of the filling volume $V_f$.

21. The sensor system according to claim 20, wherein a resistance wire loop has an electrical conductor and a low-impedance and externally electrically insulated electrical conductor electrically connected to the electrical conductor, which conductors are connected via connection points and electrical supply lines to the resistance measuring instrument.

22. The sensor system according to claim 21, wherein the electrical conductor is wound spirally around the low-impedance electrical conductor.

23. The sensor system according to claim 21, wherein the electrical conductors are applied on an electrically insulating and flexible support material, in thick-film or thin-film technology, and the flexible support material is inserted into the inner cavity of the hollow body.

24. The sensor system according to claim 1, wherein the hollow body has a double cavity, the two cavities being connected via a terminal block with two tubes for supplying or leading away substances (I) and (II).

25. The sensor system according to claim 1, wherein a pressure sensor and an adjustable valve are connected to a second hollow body to control the inner pressure in the hollow body.

26. The sensor system according to claim 1, wherein the wall of the hollow body is unsymmetrical and thus an alteration in cross-section may be generated even when the pressure difference between internal and external pressure occurs radially evenly, the unsymmetrical wall regions consisting of differing materials.

27. The sensor system according to claim 1, wherein four hollow bodies are disposed respectively offset by 90°, forming a measuring catheter.

28. The sensor system according to claim 27, wherein the measuring catheter has additional cavities for other purposes.

29. The sensor system according to claim 1, wherein, for a two-dimensional measurement of pressure distribution, a plurality of hollow bodies is disposed parallel, and the plurality of hollow bodies may be filled in succession in order to supply or lead away substances (I) and (II).

30. The sensor system according to claim 1, wherein at least two pairs of electrically conductive, oppositely-situated conductor tracks are attached on and/or in the hollow body, and the means for scanning a local cross-sectional function A(x) comprises a means for determining the resistance or the capacity of respectively one pair for determining the pressure components in different directions.

31. The sensor system according to claim 1 wherein a first and a second conductor track are disposed with differing resistances per length unit, and the electrical resistance between the one end of the first conductor track and the opposite end of the second conductor track and/or between the one end of the second conductor track and the opposite end of the first conductor track may be determined.

32. The sensor system according to claim 1, wherein substance I is a monomolecular KCl solution with a specific conductance of approximately 0.1 S/cm, or a NaCl solution.

* * * * *